US010487020B2

(12) United States Patent
Brammer et al.

(10) Patent No.: US 10,487,020 B2
(45) Date of Patent: Nov. 26, 2019

(54) METHOD FOR THE PREPARATION OF A STABILIZED ORGANOPHOSPHOROUS COMPOUND SOLUTION

(71) Applicant: Dow Technology Investments LLC, Midland, MI (US)

(72) Inventors: Michael A. Brammer, Freeport, TX (US); George R. Phillips, South Charleston, WV (US); Glenn A. Miller, South Charleston, WV (US); Donald L. Campbell, Jr., Carmel, IN (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/574,322

(22) PCT Filed: Jul. 5, 2016

(86) PCT No.: PCT/US2016/040948
§ 371 (c)(1),
(2) Date: Nov. 15, 2017

(87) PCT Pub. No.: WO2017/019259
PCT Pub. Date: Feb. 2, 2017

(65) Prior Publication Data
US 2018/0141881 A1    May 24, 2018

Related U.S. Application Data

(60) Provisional application No. 62/197,853, filed on Jul. 28, 2015.

(51) Int. Cl.
| | | |
|---|---|---|
| *C07B 63/04* | (2006.01) | |
| *C07F 9/145* | (2006.01) | |
| *B01J 31/18* | (2006.01) | |
| *C07C 45/50* | (2006.01) | |
| *C07C 215/10* | (2006.01) | |

(52) U.S. Cl.
CPC ............. *C07B 63/04* (2013.01); *B01J 31/185* (2013.01); *C07C 45/50* (2013.01); *C07C 215/10* (2013.01); *C07F 9/145* (2013.01); *B01J 2231/321* (2013.01)

(58) Field of Classification Search
CPC .......... C07B 63/04; C07F 9/145; B01J 31/185
See application file for complete search history.

(56) References Cited

U.S. PATENT DOCUMENTS

| | | | | |
|---|---|---|---|---|
| 3,703,496 A | * | 11/1972 | Hodan | ............. C07F 9/025 523/451 |
| 3,787,537 A | * | 1/1974 | De Marcq | ............. C07F 9/025 558/71 |
| 4,487,972 A | | 12/1984 | Haag et al. | |
| 4,567,306 A | | 1/1986 | Dennis et al. | |
| 4,835,299 A | | 5/1989 | Maher et al. | |
| 5,183,943 A | | 2/1993 | Bryant et al. | |
| 5,371,263 A | * | 12/1994 | Quotschalla | ............. C08K 5/17 558/71 |
| 5,449,653 A | | 9/1995 | Briggs et al. | |
| 5,728,893 A | | 3/1998 | Becker et al. | |
| 5,731,472 A | | 3/1998 | Leung et al. | |
| 5,741,942 A | | 4/1998 | Bryant et al. | |
| 5,741,943 A | | 4/1998 | Bryant et al. | |
| 5,741,944 A | | 4/1998 | Bryant et al. | |
| 5,741,945 A | | 4/1998 | Bryant et al. | |
| 5,744,649 A | | 4/1998 | Bryant et al. | |
| 5,763,679 A | | 6/1998 | Nicholson et al. | |
| 5,767,321 A | | 6/1998 | Billig et al. | |
| 5,984,640 A | | 11/1999 | Wang | |
| 7,495,134 B2 | | 2/2009 | Hess et al. | |
| 7,863,487 B2 | | 1/2011 | Eisenschmid et al. | |
| 8,008,383 B2 | * | 8/2011 | Gelbin | ............. C08J 3/21 524/128 |
| 8,461,394 B2 | | 6/2013 | Lueken et al. | |
| 2006/0224000 A1 | | 10/2006 | Papp et al. | |
| 2011/0028619 A1 | | 2/2011 | Hill et al. | |
| 2013/0225849 A1 | | 8/2013 | Berens et al. | |
| 2017/0233322 A1 | | 8/2017 | Miller et al. | |
| 2017/0240578 A1 | | 8/2017 | Phillips et al. | |

FOREIGN PATENT DOCUMENTS

| | | |
|---|---|---|
| IN | 188332 B | 9/2002 |
| WO | 1997/020798 A1 | 6/1997 |
| WO | 2012/145241 A1 | 10/2012 |

OTHER PUBLICATIONS

PCT/US2016/040948, International Search Report dated Feb. 2, 2017.
PCT/US2016/040948, Written Opinion dated Feb. 2, 2017.
PCT/US2016/040948, International Preliminary Report on Patentability dated Jan. 30, 2018.

* cited by examiner

*Primary Examiner* — Amanda L Aguirre

(57) ABSTRACT

A process involving admixing a ligand and an alkanolamine. The process allows the use of ligand despite the presence of contaminating amounts of phosphorus acid, and improves the shelf life of premixed ligand solutions.

17 Claims, No Drawings

METHOD FOR THE PREPARATION OF A STABILIZED ORGANOPHOSPHOROUS COMPOUND SOLUTION

BACKGROUND OF THE INVENTION

The invention relates to a process for the preparation of a stabilized organophosphorous composition.

Organophosphites and polyorganophosphites have been used for a variety of applications including preservatives (e.g., antioxidants) for plastic materials and as ligands for catalysts. However, phosphite ligands may decompose during long-term storage, primarily due to hydrolysis of the phosphite moiety, which produces acidic by-products that may catalyze additional degradation. Even phosphite products manufactured in high purity and packaged under stringent conditions may slowly degrade over time. Significant decomposition may require expensive reprocessing to remove the acidic by-products prior to industrial use, e.g. in a hydroformylation process, to avoid accelerated hydrolysis and/or solids formation within the production unit.

The initial acid content of the organophosphite is particularly important if the ligand is to be introduced to the end use process slowly as a solution over time, which is a common practice when it is desired to maintain the ligand concentration at a constant level. If the solid phosphite contains appreciable amounts of acid, dissolution can result in rapid hydrolysis that will consume a significant portion of the valuable ligand within days.

U.S. Pat. No. 4,835,299 discloses a method for purifying tertiary organophosphites during manufacture. Secondary organophosphite impurities are converted to primary organophosphite salts by treatment with aqueous base, and the desired tertiary organophosphite is recovered via crystallization. That process may be appropriate for reprocessing of partially decomposed ligand, but it is not suitable for routine use in a hydroformylation facility, and doesn't address storage of ligand solutions.

US 2013/0225849 discloses the use of trace amounts of sodium methoxide as an additive in a washing step during the purification phase of the ligand manufacturing process to address the instability of polyorganophosphites in the presence of residual solvent. However, the presence of such an extremely strong base is not suitable in many catalytic processes, such as hydroformylation, hydrocyanation or hydrogenation. US 2013/0225849 also teaches that the strong base is removed prior to packaging.

WO 2012/145241 teaches how to store active transition metal-ligand catalyst solutions by reducing water or acid content prior to storage using an extractor.

U.S. Pat. No. 8,461,394 describes the use of hindered amines, e.g. piperidines, to stabilize bisphosphite-promoted hydroformylation processes. For example, the bisphosphite and amine are combined for daily additions. Insoluble salts are formed and filtered away. Employing such a process with ligand that is already significantly degraded would generate large amounts of insoluble salts that could plug lines and degrade pumps. The addition of the amine/ligand solution to the hydroformylation reaction system is immediate, and no teaching about the long term stability of such a mixture is presented.

Hydrolyzable organophosphorus ligands employed for hydroformylation must be added to the process at a rate comparable to their degradation rate, as taught in, e.g., U.S. Pat. Nos. 5,741,945, 5,741,943 and 7,863,487.

The organophosphorous ligand may be added in a batch manner; for example, the solid ligand may be added to a separate vessel, e.g., a mix tank, dissolved in product aldehyde and added to the process within a single day. Even over a short period of time, hydrolytic degradation can occur if the organophosphorous compound added to the mix tank contains significant levels of acid. Hydrolysis can be exacerbated by high levels of water or carboxylic acids, which can form in aldehydes upon exposure to air. Because hydrolysis results in acid by-products, an autocatalytic scenario could potentially develop wherein the bulk of the expensive ligand is consumed before it ever reaches the hydroformylation process.

In other cases, it is advantageous to add the ligand to the process on a continuous basis. In one method, the ligand and aldehyde product are combined in the mix tank, and the resulting solution metered into the system at an appropriate rate. Effective implementation of a continuous addition strategy requires storage of the ligand solution in the mix tank for extended periods, e.g., days, weeks or even longer. Stability of the solution is impacted by both the acid content and the extended time in storage, thus a constant ligand addition strategy presents a greater risk for excessive ligand degradation.

Accordingly, there is a need for an easy, cost-effective means to utilize hydrolyzable organophosphorus ligands, which have partially degraded during storage, within a hydroformylation process, and to add that ligand as a solution over time without excessive degradation of the valuable ligand compound.

SUMMARY OF THE INVENTION

The process of the invention comprises preparing a solution from raw materials comprising a solvent, an alkanolamine and a ligand raw material comprising a hydrolyzable organophosphorus ligand, wherein the raw materials have a total acidity equivalent to at least 200 ppmw phosphorous acid, based on the weight of the ligand, wherein the concentration of alkanolamine in the solution is from 0.025 to 1 wt % based on the total weight of the solution, and wherein the solution is substantially free of transition metals.

Surprisingly, the addition of the alkanolamine will stabilize solutions of hydrolyzable organophosphorous ligands dissolved in product aldehyde for relatively long periods, e.g., over a week or more, even if the aldehyde is saturated with water and the ligand or ligand solution, contains high initial concentrations of acidic compounds. The process may allow one to avoid the costs associated with reprocessing partially degraded ligand, may greatly reduce the loss of ligand in the mix tank, and may prevent the formation of precipitates within the homogeneous hydroformylation process.

DETAILED DESCRIPTION OF THE INVENTION

The process of the invention employs a hydrolyzable organophosphorous ligand, a solvent and an alkanolamine.

As used herein, the term "mix tank" means a vessel that is used to mix ligand, and optionally other catalyst precursor materials, with a solvent to prepare a catalyst solution.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

A hydrolyzable organophosphorous ligand is a trivalent phosphorous compound that contains at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligand may include chelate structures and/or may contain multiple P—Z moieties such as polyphosphites, polyphosphoramidites, etc. and mixed P—Z moieties such as phosphite-phosphoramidites, flurophosphite-phosphites, and the like. Examples of phosphite ligands include mono-organophosphite, diorganophosphite, triorganophosphite and organopolyphosphite compounds. Such organophosphorous compounds and methods for their preparation are well known in the art. Mixtures of hydrolyzable organophosphorous ligands can be employed. The type of hydrolyzable organophosphorous ligands employed in this invention are described in detail in U.S. Pat. No. 7,863,487, the teachings of which are incorporated herein by reference.

The phosphorous acid content of the ligand raw material is at least 200 ppmw, or at least 300 ppmw, based on the weight of the ligand. A hydrolyzable organophosphorous ligand that has partially degraded during storage may be effectively utilized as the ligand raw material for the process of the invention.

The alkanolamine is a compound that serves to increase the storage stability of the hydrolyzable organophosphorous ligand in solution. Advantageously, the alkanolamine comprises at least one compound selected from the alkanolamines described hereinbelow. Mixtures of alkanolamines can be employed. In various embodiments of the invention, the alkanolamine concentration is from 0.025 to 1 wt %, or from 0.3 to 0.7 wt %, or from 0.025 to 0.7 wt %, or from 0.3 to 1 wt %, based on the total weight of the solution.

Examples of alkanolamines include those with the structure:

(IX)

wherein $R^{32}$, $R^{33}$, and $R^{34}$ represent H, alkyl or aryl substituents, provided that no more than one of $R^{32}$, $R^{33}$, and $R^{34}$ can be hydrogen, while preferably none are hydrogen, and preferably at least 1 is an electron withdrawing substituent, and most preferably 2 are electron withdrawing substituents. The electron withdrawing substituent advantageously is an electron withdrawing alkyl or aryl substituent, and examples of these include alkyl-substituted or unsubstituted aryl moieties, halogenated, alkoxylated, alkylalkoxylated, or carboxylated aryl moieties, beta-alkoxy or beta-alkoxyalkyl moieties (such as beta-hydroxyethyl, beta-hydroxy-alpha-methylethyl, beta-hydroxy-beta-methylethyl, and ethoxylated and/or propoxylated adducts thereof). Preferred alkanolamines of the preceding formula include triethanolamine (TEA), triisopropanolamine, methyldiethanolamine, dimethylethanolamine and ethyldiethanolamine Ethoxylates and propoxylates of the alkanolamine can also be employed. Mixtures of alkanolamines can be employed.

The solvent is a material that serves to dissolve the ligand and the alkanolamine Advantageously, the solvent is compatible with the end use process in which the ligand solution will be employed, e.g., a hydroformylation process. For example, if the end use is a hydroformylation process where the product is an aldehyde, that aldehyde can be employed as the solvent in the process of the invention. Solvents are well known, and are described for example in U.S. Pat. Nos. 5,728,893 and 5,874,640. Examples of suitable solvents include aromatic hydrocarbons (such as toluene or xylene) ethers (such as tetrahydrofuran, tetraglyme, or diphenyl ether) and esters (such as 2,2,4-trimethyl-1,3-pentanediol monoisobutyrate, ethyl acetate or isononyl benzoate), and aldehydes such as butyraldehyde, valeraldehyde, which are preferred.

The solvent advantageously is employed in an amount that is sufficient to allow a solution of the ligand and the alkanolamine to be prepared. The concentration of the ligand in the solution is not critical, and the upper limit is determined primarily by the solubility limit of the ligand in the solvent. Advantageously, the solvent is a liquid at standard temperature and pressure. Mixtures of solvents can be employed.

Carboxylic acids form in situ in the solvent upon exposure to oxygen, including air. Thus, in one embodiment of the invention, the solvent raw material has a carboxylic acid content of 0.02 to 1 wt %, based on the weight of the solvent. The amount of alkanolamine can be adjusted to account for this acid content in order to neutralize the acid content of the solvent.

In one embodiment of the invention, the solution is prepared by mixing the alkanolamine with the hydrolyzable organophosphorous ligand and the solvent in a mix tank. In one embodiment of the invention, the solids are added to the mix tank and then air is removed, e.g., via $N_2$ purge or vacuum/$N_2$ refill, prior to charging the solvent to avoid oxidation of the ligand. Rhodium compounds may optionally be added. Once the desired components are present, the mixing can be achieved according to methods, and using equipment, well known to those skilled in the art. For example, the mixing may be conducted in a simple stirred tank that is not subject to the pressures and temperatures found in reaction vessels. Agitation may be provided by circulation induced by an agitator, a pump, or other know agitation means. In various embodiments of the invention, the ligand solution comprises, consists essentially of, or consists of, the hydrolyzable organophosphorous ligand, the solvent, and the alkanolamine.

In one embodiment of the invention, a preliminary solution of the ligand raw material and the solvent is prepared, then the alkanolamine is added to that solution. The preliminary solution of the ligand in the solvent can contain a total acidity from any source, including the solvent, reported as phosphorous acid, of at least 200 ppmw, or at least 300 ppmw, based on the weight of the solution.

After treatment by the process of the invention, solid ligand that originally contained 200-10,000 ppm of phosphorous acid may be stored for days with no significant additional degradation.

A preferred method of analyzing the solid ligand for initial acid content is by ion chromatography, which detects ions present in an aqueous sample. Although phosphorous acid is quite soluble in water, many solid ligands are not;

thus, a sample preparation step comprising an aqueous extraction may be required. The aqueous solution employed in the extraction may comprise, in addition to water, a base or a buffer in relatively low concentrations, as known to those skilled in the art. The sample preparation may consist of thoroughly contacting the solid ligand with the aqueous solution, filtering away the insoluble ligand and analyzing the filtrate. Advantageously, the solid sample may also be dissolved in an organic solvent that is immiscible with water prior to extraction. Examples of suitable organic solvents include toluene, xylene, and the like. This sample preparation comprising dissolution/extraction has the advantage of allowing acids that may be trapped inside the crystalline lattice or otherwise not easily extracted to be measured more effectively.

Methods to measure acidity in solutions are well known and include titration and pH measurement of an aqueous extraction of the solution using pH meters or pH indicating paper strips. The method should detect all sources of acids such as carboxylic acids, phosphorous acid, phosphoric acid, and the like with pKa values below 6.0. Since the exact nature of the acidic species is not clear, the acidity equivalent is reported as wt %, or ppmw, phosphorous acid. For the purposes of this invention, the term "wt % phosphorous acid" will encompass any source of acidity.

The ligand solution can be used in a wide range of applications where hydrolyzable organophosphorous ligands are employed. The solution is especially useful for applications in which a hydrolyzable organophosphorous ligand solution is to be stored for extended periods of time. For example, a ligand solution can be employed in a hydroformylation, hydrocyanation, and/or hydrogenation process.

The rate of ligand decomposition is presumed to be related to the exposure of the P(III) moiety to oxygen and moisture. Accordingly, well-known measures to avoid exposure to an adverse atmosphere are advantageously employed during preparation and storage of the ligand solution. In one embodiment of the invention, at least a portion of the ligand solution is used, e.g., fed to the hydroformylation process, immediately after the solution is formed. In various embodiments of the invention, at least a portion of the ligand solution is stored for a period of at least 1 hour, at least 12 hours, at least 1 day, at least 2 days, at least 10 days, at least 30 days, or at least 60 days. In many cases, the ligand solution will be stored for from 1 to 30 days. The solution is generally stored at ambient temperature, and preferably is stored at a temperature that is greater than 0° C. and not more than 35° C.

The progress of decomposition or degradation of an organophosphorous ligand in solution can be determined by $^{31}$P NMR or high pressure liquid chromatography (HPLC).

The hydroformylation process, and conditions for its operation, are well known. A hydroformylation process may be conducted in any batch, continuous or semi-continuous fashion and may involve any catalyst liquid and/or gas recycle operation desired. The resulting aldehydes may be further processed to useful products or intermediates for other products such as alcohols, acids, esters (plasticizers), or the like on a commercial scale.

The use of an aqueous extraction zone to prevent and/or lessen hydrolytic degradation of the organophosphite ligand and deactivation of a metal-organophosphite ligand complex within hydroformylation reaction fluid is disclosed in U.S. Pat. Nos. 5,741,942, 5,741,944, and copending application PCT/US15/019560. In one embodiment of the invention, the ligand, the alkanolamine and, optionally, the catalytic metal, are charged to the catalyst mix tank, dissolved in aldehyde and subsequently passed through an aqueous extraction zone prior to entering the hydroformylation reaction zone. Adding the alkanolamine/ligand solution upstream of an aqueous extraction zone allows degradation by-products to be removed before they enter the reaction zone. Following contact with the aqueous solution in the extraction zone, the ligand solution is introduced to the hydroformylation system at one or more points such as, for example, one or more of the reaction zones (reactors).

Illustrative metal-organophosphorous ligand complex catalysts employable in such hydroformylation, hydrocyanation, and/or hydrogenation reactions, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

Specific Embodiments of the Invention

All parts and percentages in the following examples are by weight unless otherwise indicated.

The butyraldehyde product is employed as a solvent, and is stirred with excess water prior to use, and the resulting water concentration is determined by Karl-Fischer titration (1.3-1.5 wt % water).

Ligand concentration is monitored by reverse-phase HPLC (external standard calibration method). Samples are stored in septum-capped vials under nitrogen. Slow evaporation of aldehyde results in a slight increase in ligand concentration in some long-term samples.

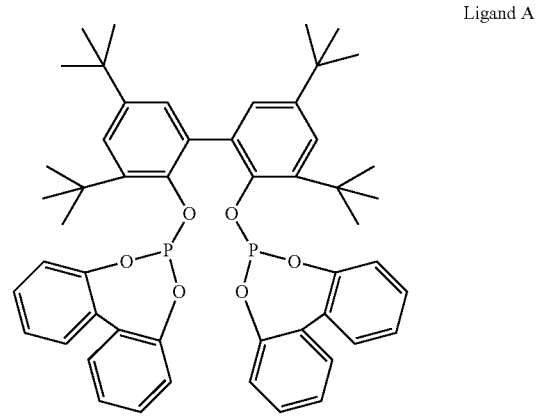 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1]

Ligand A

Initial phosphorous acid content of Ligand A is determined by ion chromatography (IC) using a Dionex ICS 2100 ion chromatograph with eluent generation and suppressed conductivity detection including a carbonate removal device. The chromatograph is fitted with an IonPac AG11-HC Guard Column and an IonPac AS11-HC Analytical Column Data analysis is performed with Chromeleon 7.0 software. Samples are prepared by aqueous extraction of the solid ligand (0.5 to 1 g) with deionized water (10-15 mL), or by dissolution of the solid ligand (0.1 to 0.5 g) in toluene (5 mL) followed by extraction of the toluene solution with aqueous sodium hydroxide (0.004 M; 12-15 mL). Samples containing very high levels of acid require additional dilution of the aqueous extract to stay within the calibration range.

Comparative Experiments 1-6—(Not Embodiments of the Invention)

20 mL glass vials are charged with solutions of Ligand A in butyraldehyde (2 to 2.5 wt % ligand A). The initial amounts of phosphorous acid are determined by IC, with samples prepared via direct aqueous extraction of Ligand A solids. The resulting values are shown in Table 1. The solutions are stirred at room temperature and sampled periodically for HPLC to determine Ligand A concentration. The results are shown in Table 1.

TABLE 1

| Comparative Experiment | phosphorous acid (ppm) | % ligand A remaining after: | | | |
|---|---|---|---|---|---|
| | | 1 day | 2 days | 3 days | 6 days |
| 1 | 2 | 95.9 | 94.6 | 91.0 | 102.0 |
| 2 | 322 | 96.7 | 93.8 | 89.6 | 80.8 |
| 3 | 403 | 94.0 | 90.9 | 87.6 | 67.8 |
| 4 | 717 | 89.2 | 84.7 | 78.2 | 61.3 |
| 5 | 1193 | 91.2 | 83.1 | 76.7 | 49.6 |
| 6 | 3800 | 83.4 | 69.6 | 62.7 | 36.5 |

The data clearly shows a direct correlation between the beginning acid content and the degradation rate of Ligand A.

Examples 1-6

The procedure of Comparative Experiments 1-6 is followed except that sufficient triethanolamine is added to the solutions to prepare new solutions containing 1 wt % TEA. The results are shown in Table 2.

TABLE 2

| Example | phosphorous acid (ppm) | % ligand A remaining after: | | | |
|---|---|---|---|---|---|
| | | 1 day | 2 days | 3 days | 6 days |
| 1 | 2 | 94.7 | 93.0 | 93.7 | 98.5 |
| 2 | 322 | 98.7 | 97.6 | 99.1 | 99.1 |
| 3 | 403 | 98.6 | 95.6 | 93.2 | 90.5 |
| 4 | 717 | 90.3 | 85.2 | 83.6 | 90.5 |
| 5 | 1193 | 98.8 | 93.1 | 92.1 | 85.5 |
| 6 | 3800 | 99.1 | 97.1 | 96.1 | 101.4 |

Examples 7-12

The procedure of Examples 1-6 is followed except that 0.5 wt % triethanolamine solutions are employed. The results are shown in Table 3.

TABLE 3

| Example | phosphorous acid (ppm) | % ligand A remaining after: | | | |
|---|---|---|---|---|---|
| | | 1 day | 2 days | 3 days | 4 days |
| 7 | 2 | 101.0 | 100.4 | 101.4 | 101.8 |
| 8 | 322 | 98.3 | 97.8 | 99.2 | 98.7 |
| 9 | 403 | 100.0 | 100.4 | 99.8 | 99.9 |
| 10 | 717 | 98.5 | 98.6 | 99.8 | 100.2 |
| 11 | 1193 | 98.8 | 98.7 | 100.9 | 98.9 |
| 12 | 3800 | 98.5 | 98.8 | 100.9 | 98.6 |

Examples 13-18

The procedure of Examples 1-6 is followed except that 0.25 wt % triethanolamine solutions are employed. The results are shown in Table 4.

TABLE 4

| Example | phosphorous acid (ppm) | % ligand A remaining after: | | | |
|---|---|---|---|---|---|
| | | 1 day | 2 days | 3 days | 4 days |
| 13 | 2 | 95.9 | 91.0 | 86.3 | 88.7 |
| 14 | 322 | 87.3 | 82.0 | 73.8 | 74.3 |
| 15 | 403 | 86.9 | 85.2 | 83.4 | 85.7 |
| 16 | 717 | 97.3 | 84.6 | 82.6 | 85.5 |
| 17 | 1193 | 78.9 | 64.3 | 64.3 | 65.0 |
| 18 | 3800 | 82.6 | 81.4 | 81.6 | 80.5 |

Examples 19-24

The procedure of Examples 1-6 is followed except that 0.025 wt % triethanolamine solutions are employed. The results are shown in Table 5.

TABLE 5

| Example | phosphorous acid (ppm) | % ligand A remaining after: | | | |
|---|---|---|---|---|---|
| | | 1 day | 2 days | 3 days | 4 days |
| 19 | 2 | 92.8 | 88.3 | 85.8 | 82.6 |
| 20 | 322 | 90.5 | 86.7 | 82.8 | 88.2 |
| 21 | 403 | 86.9 | 83.7 | 80.8 | 86.8 |
| 22 | 717 | 84.9 | 84.3 | 82.4 | 91.3 |
| 23 | 1193 | 89.4 | 83.3 | 80.8 | 85.2 |
| 24 | 3800 | 88.7 | 79.1 | 71.5 | 49.7 |

Comparative Experiments 7-12—(Not Embodiments of the Invention)

The procedure of Comparative Experiments 1-6 is followed, except that the IC samples are prepared via the toluene dissolution/aqueous extraction method. The results are shown in Table 6.

TABLE 6

| Comparative Experiment | phosphorous acid (ppm) | % ligand A remaining after: | | | | |
|---|---|---|---|---|---|---|
| | | 1 day | 2 days | 3 days | 6 days | 20 days |
| 7 | 57 | 101.7 | 113.1 | 99.9 | 106.4 | |
| 8 | 561 | 97.9 | 98.0 | 92.4 | 84.2 | |
| 9 | 1712 | 101.0 | 98.4 | 90.8 | 73.6 | 1.0 |
| 10 | 3858 | 96.2 | 98.3 | 83.2 | 54.8 | |
| 11 | 5910 | 93.6 | 84.3 | 70.6 | 31.9 | 0.1 |
| 12 | 9630 | 77.5 | 60.4 | 45.6 | 11.0 | |

A direct correlation between the beginning acid content and the degradation rate of Ligand A is clearly demonstrated.

Examples 25-30

The procedures of Comparative Experiments 7-12 are followed except that 0.5 wt % triethanolamine solutions are employed. The results are shown in Table 7.

TABLE 7

| Example | phosphorous acid (ppm) | % ligand A remaining after | | | | |
|---|---|---|---|---|---|---|
| | | 1 day | 2 days | 3 days | 6 days | 20 days |
| 25 | 57 | 101.3 | 101.0 | 99.2 | 106.5 | |
| 26 | 561 | 100.6 | 105.3 | 99.8 | 114.3 | |
| 27 | 1712 | 103.4 | 103.8 | 100.0 | 114.3 | 119.5 |
| 28 | 3858 | 103.9 | 101.8 | 97.2 | 104.3 | |
| 29 | 5910 | 100.5 | 103.0 | 105.6 | 110.6 | 110.8 |
| 30 | 9630 | 107.9 | 100.6 | 98.1 | 102.5 | |

The examples clearly show a significant benefit upon addition of triethanolamine relative to the Comparative Experiments 7-12. Even the significantly degraded material, e.g., Examples 29 and 30, which would ordinarily require expensive reprocessing prior to industrial use, may be effectively utilized by employing the process of the invention. Moreover, Examples 27 and 29 demonstrate that a ligand solution of the invention may be effectively stored for extended periods (e.g., >20 days).

What is claimed is:

1. A process comprising: preparing a solution from raw materials comprising a solvent, an alkanolamine and a ligand raw material comprising a hydrolyzable organophosphorus ligand, wherein degradation by-products in the solution have a total acidity equivalent to at least 200 ppmw phosphorous acid, based on the weight of the ligand, wherein the concentration of alkanolamine in the solution is from 0.025 to 1 wt % based on the total weight of the solution, and wherein the solvent is an aromatic hydrocarbon, an ether, an ester, an aldehyde, and/or an alcohol.

2. The process of claim 1 wherein the ligand raw material is a solid ligand, and comprises greater than 200 ppmw phosphorous acid.

3. The process of claim 1 wherein the solvent comprises an alcohol and/or aldehyde.

4. The process of claim 1 wherein the concentration of the alkanolamine is from 0.2 to 0.7 wt % based on the total weight of the solution.

5. The process of claim 1 wherein the alkanolamine includes at least one compound selected from triethanolamine, triisopropanolamine, methyldiethanolamine, dimethylethanolamine and ethyldiethanolamine.

6. The process of claim 1 wherein the alkanolamine includes at least one compound selected from triethanolamine and triisopropanolamine.

7. The process of claim 1 wherein the alkanolamine is triethanolamine.

8. The process of claim 1 further comprising feeding the ligand solution to a hydroformylation process.

9. The process of claim 8 wherein the hydroformylation process comprises a reaction zone and an extraction zone, and wherein at least a portion of the solution is fed from a mix tank to the reaction zone and/or the extraction zone of the hydroformylation process.

10. The process of claim 8 wherein the solution is fed to the extraction zone.

11. The process of claim 8 wherein the hydroformylation process comprises contacting CO, $H_2$, and at least one olefin under hydroformylation conditions sufficient to form at least one aldehyde product in the presence of a catalyst comprising, as components, a transition metal and the hydrolyzable ligand.

12. The process of claim 8 wherein the solution is stored for more than a day before being used in an end use application.

13. The process of claim 8 wherein the solution is stored for more than 3 days before being used in an end use application.

14. The process of claim 8 wherein the solution is stored for a period of at least 30 days before being used in an end use application.

15. The process of claim 1 wherein the solvent has a carboxylic acid content of from 0.02 to 1 weight percent, based on the weight of the solvent.

16. The process of claim 1, wherein the solution is free of transition metals.

17. A process comprising: preparing a solution from raw materials comprising a solvent, an alkanolamine and a ligand raw material comprising a hydrolyzable organophosphorus ligand, wherein degradation by-products in the solution have a total acidity equivalent to at least 200 ppmw phosphorous acid, based on the weight of the ligand, wherein the concentration of alkanolamine in the solution is from 0.025 to 1 wt % based on the total weight of the solution, and wherein the solvent is xylene, toluene, an ether, an ester, an aldehyde, and/or an alcohol.

* * * * *